(12) United States Patent
Gonry et al.

(10) Patent No.: US 8,986,716 B2
(45) Date of Patent: Mar. 24, 2015

(54) FRUCTAN-BASED EPILATORY COMPOSITIONS

(75) Inventors: Patrick Gonry, Antwerp (BE); Karl Booten, Geetbets (BE)

(73) Assignee: Beneo-Orafti S.A. (BE)

( * ) Notice: Subject to any disclaimer, the term of this patent is extended or adjusted under 35 U.S.C. 154(b) by 837 days.

(21) Appl. No.: 12/530,432

(22) PCT Filed: Mar. 4, 2008

(86) PCT No.: PCT/EP2008/001691
§ 371 (c)(1),
(2), (4) Date: Dec. 16, 2009

(87) PCT Pub. No.: WO2008/107153
PCT Pub. Date: Sep. 12, 2008

(65) Prior Publication Data
US 2010/0092528 A1  Apr. 15, 2010

(30) Foreign Application Priority Data
Mar. 7, 2007  (EP) .................................... 07004650

(51) Int. Cl.
*A61Q 9/04* (2006.01)
*A61K 9/70* (2006.01)
*A61K 31/715* (2006.01)
*A61K 8/73* (2006.01)

(52) U.S. Cl.
CPC ... *A61Q 9/04* (2013.01); *A61K 8/73* (2013.01); Y10S 514/844 (2013.01)
USPC .......... 424/401; 424/70.1; 424/73; 424/78.02; 514/54; 514/844; 8/160

(58) Field of Classification Search
None
See application file for complete search history.

(56) References Cited

U.S. PATENT DOCUMENTS

| 4,842,610 | A  | * | 6/1989  | Gordon et al. ..................... 8/160 |
| 6,207,176 | B1 | * | 3/2001  | Howard et al. ................ 424/402 |
| 6,696,067 | B2 | * | 2/2004  | Brandt et al. ................. 424/401 |
| 7,151,079 | B2 | * | 12/2006 | Fack et al. ..................... 510/121 |
| 2003/0186934 | A1 | * | 10/2003 | Rathjens et al. ................. 514/54 |
| 2004/0016435 | A1 |   | 1/2004  | Deem et al. .............. 108/207.14 |
| 2004/0081633 | A1 | * | 4/2004  | Mercier et al. ............. 424/70.12 |
| 2004/0161435 | A1 | * | 8/2004  | Gupta ........................... 424/401 |
| 2006/0276369 | A1 |   | 12/2006 | Levecke et al. ............... 510/470 |
| 2007/0098663 | A1 | * | 5/2007  | Gupta ........................ 424/70.13 |

FOREIGN PATENT DOCUMENTS

| CA | 2289879         | 5/2001 | ............. A61K 7/155 |
| DE | 10247696        | 4/2004 | ............... A61K 8/73 |
| EP | 1541117         | 6/2005 | ............... A61K 7/06 |
| FR | 2267755         | 4/1974 | ............... A61K 7/14 |
| FR | 2798064         | 3/2001 | ............. A61K 7/155 |
| HU | 0402393         | 1/2007 | ............... A61K 8/60 |
| WO | WO 2005058258 A1 * | 6/2005 | |

OTHER PUBLICATIONS

Banguela, A. and Hernandez, H. Fructans: from natural sources to transgenic plants. Biotecnologia Aplicada 2006, 23: 202-210.*
Product data sheet for Frutafit CLR downloaded from the site: http://www.qaa.com.co/productos/download/otros/fibra/pds_frutafitr_clr.pdf on Mar. 6, 2012.*
Product data sheet for Frutafit HD downloaded from the site: http://www.qaa.com.co/productos/download/otros/fibra/pds_frutafitr_hd.pdf on Mar. 6, 2012.*
Blanchard, P.H. and Katz, F.R. Starch Hydrolysates, from Food Polysaccharides and Their Appliations, Edited by Alistair M . Stephen , Glyn O . Phillips , and Peter A . Williams. CRC PRess, 2006, pp. 119-145.*
Paul H. Blanchard and Frances R. Katz. "Starch Hydrolysates" in Food Potysaccharides arld Their Applications, Edited by Alistair M . Stephen, Glyn O. Phillips , arld Peter A . Wiliams. CRC Press 2006, pp. 120-145.*
European Communication, Appln. No. 08 716 210.3 1521 (5 pgs) dated Apr. 16, 2010.

* cited by examiner

*Primary Examiner* — Frederick Krass
*Assistant Examiner* — Michael P Cohen
(74) *Attorney, Agent, or Firm* — Hayes Soloway P.C.

(57) ABSTRACT

The invention relates to an epilatory mixture comprising a fructan, preferably inulin. Furthermore, an epilatory composition is disclosed comprising said epilatory effective mixture. Also a method of use of said epilatory composition of the invention for the removal of unwanted hair from the skin is disclosed, as well as a method of use of said composition for carrying out an epilatory treatment which can be carried out by a professional person as well as by a non-professional person.

29 Claims, No Drawings

FRUCTAN-BASED EPILATORY COMPOSITIONS

FIELD OF THE INVENTION

The present invention relates to an epilatory mixture comprising at least one carbohydrate, to a composition comprising same, to their manufacture, and to a method of use of same.

BACKGROUND AND PRIOR ART

A characteristic of the human skin is the presence of hair of which the appearance and nature usually differ according to the area on the skin. Depending from various circumstances, hair on the scalp is commonly highly wanted, whereas hair at other area's of the skin is often unwanted for various reasons, including for example beauty reasons, reasons of convenience, hygienic and medical reasons. Historically a few major methods for removal of undesired skin hair have been developed, namely shaving, depilation (hair removal by means of a chemical hair degradation process) and epilation (hair removal by pulling out unwanted hair by a purely mechanical method). All these methods present advantages and drawbacks.

Shaving with any type of razor blade, typically used for removal of beard hair, is often not suitable for removal of hair at other area's such as armpits, pubis and legs, and it presents the danger of cuts which in turn can lead to infections of these wounds. Shaving with an electric razor avoids cuts but may leave a dry skin and sometimes may lead to mechanical skin irritation. Depilation is also widely applied but is often provoking a highly undesirable chemical irritation of the skin.

Epilation presents the advantage that together with the hair also the hair bulb (hair papilla) is removed. This results in an increased lasting effect of the epilation because it takes longer for the hair to grow and to become visible again.

Epilatory compositions, which term as used herein has the usual meaning of a composition used to achieve hair removal by primarily mechanical means; typically belong to one or more of the following conventional types: adhesive strips, hot wax, cold wax, and sugar wax. An epilatory composition contains or may even essentially consist of an epilatory mixture; the term epilatory mixture as meant herein means that portion—or, in case an epilatory composition contains several epilatory mixtures: those portions—of an epilatory composition that actually achieve the desired epilatory function.

Adhesive strips often suffer from the drawback that either all the unwanted hair is not properly removed because it is insufficiently sticking to the adhesive on the strip, or, when the adhesive properties of the adhesive are increased, the skin is damaged when the adhesive strip is removed from the skin.

Hot wax compositions are already in use for centuries. Typically they are based on rosin wax, paraffin wax and/or beeswax. The wax composition is warmed up to become molten, is applied to the skin and then allowed to cool, forming a solid layer in which the hair is caught. Accordingly, the caught hair is removed from the skin when the solid wax layer is pulled off of the skin. Precautions for the application of hot wax on the skin are necessary to avoid burns, and good skills are required to obtain satisfactory epilatory results without damaging the skin. Furthermore, residues of the wax on the skin have usually to be removed by means of a solvent or oil.

Cold wax compositions largely correspond to hot wax compositions but typically comprise further components that ensure a pliable structure of the wax layer on the skin which improves the ease and comfort of the epilatory treatment. Removal of wax residues from the skin usually requires treatment with a solvent or oil too.

Epilatory mixtures comprising at least one carbohydrate, such as sugar waxes, commonly classified, depending from the temperature at which they are applied to the skin, as warm sugar waxes or as cold sugar waxes, are also in use already for centuries. They are typically based on sucrose and/or fructose as the main adhesive components. Warm sugar waxes are somewhat more efficient to remove unwanted skin hair than cold sugar waxes, but they suffer from the typical drawbacks of warm waxes, such as causing possible skin burns when not properly applied. Accordingly, cold sugar waxes are often preferred for epilatory treatments.

Various sugar-based epilatory compositions have already been covered by several patent applications and patents.

FR 2267755 discloses an epilatory composition for cold application composed of a mixture of the carbohydrates sorbitol, glucose and sucrose which have been dissolved in water under heating at a temperature below the caramelisation temperature of the sugar, and that further comprises glycerine and proteins which provide a softening effect to the skin. The composition, comprising about 72% carbohydrates (% dry matter), presents good adhesion to the skin and hair, and does not form a rigid mass when applied to the skin.

FR 2798064 discloses an epilatory composition for cold application comprising at least one sugar such as sucrose, fructose, glucose, honey, sugar syrup, and an additive that enhances the adhesion of the sugar to the hair on the skin. Typical additives include hydrogenated colophane, silicon polymers, proteins, and carbohydrates from plant origin such as starch.

CA 2289879 discloses an epilatory composition for cold application comprising sucrose, corn syrup, corn starch, citric acid and water, which forms a pliable cold layer on the skin, enabling removal of the hair from the skin when the layer is pulled off.

HU 0402393 A1 (XP-002448216) discloses a depilation paste that contains fructose, glucose and water, and does not contain acid.

EP 1541117 A discloses cosmetic rinse-off compositions comprising inulin-type fructan. The inulin-type fructan can be used to completely substitute cationic polymeric conditioning agents in conventional cosmetic rinse-off compositions.

DE 10247696 discloses cosmetic or dermatological emulsions, containing a combination of (a) a saccharide-N-alkylurethane; and (b) one or more surfactants, optionally together with (c) further cosmetic and/or dermatological agents or auxiliaries.

An advantage provided by sugar waxes, particularly warm sugar waxes, is that by means of these waxes the removal of undesired hair is rather easy and efficient, and that their use seldom leads to chemical skin irritation. Furthermore, residues from sugar wax on the skin can easily be removed with water or water and soap. Accordingly, sugar-based epilatory compositions are gaining increasing interest.

Furthermore, over the last years there is a strong increase in the trend to remove undesired hair, largely for beauty reasons. Consequently, there is a high increase in epilatory treatments, in particular in the use of sugar-based epilatory waxes by professionals as well as by non-professional people.

Accordingly, there is a need for epilatory waxes which have a high functionality in hair removal yet do not suffer from the disadvantages of known sugar-based waxes such as the need for hot application to the skin. As a result thereof, there is an ongoing search for alternative and/or improved sugar-based epilatory compositions.

OBJECT OF THE INVENTION

One object of the present invention is the provision of an alternative epilatory mixture and composition comprising same. Another object of the present invention is the provision of an improved epilatory mixture and composition comprising same. Still a further object is the provision of a method of use of said mixture and composition for removing unwanted hair from the skin.

DESCRIPTION OF THE INVENTION

Said and other objects are realised by the present invention, described in detail and claimed below.

During the search for alternative and/or improved sugar-based epilatory compositions, it has been found that carbohydrate-containing epilatory mixtures comprising a fructan present excellent epilatory performances, while not presenting the drawbacks of known sugar-based epilatory compositions, particularly of warm sugar-based waxes. Said findings and compositions constitute the basis of the present invention.

Accordingly, the present invention relates to epilatory mixtures comprising at least one carbohydrate, wherein the carbohydrate comprises a fructan.

An advantage of the epilatory mixture according to the invention is that a very good epilatory function can be achieved without having to resort to high application temperatures.

Within the context of the present invention, the terms carbohydrate and saccharide are synonyms and have their common meaning.

The term fructan as used herein has its common meaning of being a generic term that relates to a polydisperse carbohydrate material consisting mainly of fructosyl-fructose links with optionally a glucose starting moiety. The meaning of fructan encompasses the more specific compounds inulin—wherein the fructosyl-fructose links are mainly of the β(2→1) type—and levan—wherein the fructosyl-fructose links are mainly of the β(2→6) type. Both inulins and levans can be linear or branched. The meaning of the term inulin on its part encompasses the compounds known as oligofructoses; typical of oligofructose is that the degree of polymerisation (DP) ranges from 2 to 10.

The degree of polymerisation (DP) of the fructans used in the epilatory mixture of the invention can vary within wide limits; preferably, the DP ranges from 2 to 75, more preferably from 2 to 30, 2 to 12 or even from 2 to 9. In a preferred embodiment of the invention, the fructan in the epilatory mixture comprises or even consists essentially of inulin.

It was found that the presence of a significant amount of fructan is instrumental in the present invention in achieving the desired epilatory function. The epilatory mixture of the invention, therefore, preferably comprises between 10 and 85 wt. % of fructan. The weight percentage as indicated here relates to the epilatory mixture as a whole, and refers to the dry matter content of the fructan. More preferably, the epilatory mixture of the invention comprises between 25 and 82 wt. % or between 35 and 79 wt. % or between 45 and 76 wt. % of a fructan, whereby the fructan is preferably inulin, more preferably oligofructose.

In a preferred embodiment of the invention, the epilatory mixture as a whole comprises between 1 and 45 wt. % of at least one separately added monosaccharide or disaccharide. This has the advantage that the viscosity of the epilatory mixture can be controlled more precisely. The phrasing 'separately added' is understood to meant that those monosaccharides and/or non-fructan disaccharides that are comprised in fructan products that are commercially supplied are not taken into account in calculating the amount of monosaccharide or disaccharide. Preferably, the at least at least one separately added monosaccharide or disaccharide comprises fructose and/or saccharose; this has the advantage that compatibility with the fructan is ensured.

In a further preferred embodiment of the invention, the epilatory mixture as a whole comprises between 0.5 and 15 wt. % of a $C_1$-$C_{12}$ diol. Such compounds are as such known. Preferably, the $C_1$-$C_{12}$ diol has a solubility in water of at least 0.5 wt. % at room temperature. Preferred examples of the $C_1$-$C_{12}$ diol include $C_3$ diols, $C_4$ diols, $C_5$ diols and $C_6$ diols; methylpropanediol is particularly preferred. It was found that the addition of a $C_1$-$C_{12}$ diol has as advantage that a further control of viscosity and/or adhesive force of the epilatory mixture can be achieved. In particular it was found that such control of viscosity and adhesive power is even more optimal in case the epilatory mixture as a whole comprises or also comprises between 1 and 25 wt. % water. It is thus preferred that in the epilatory mixture of the invention the sum of water and the $C_1$-$C_{12}$ diol amounts to between 10 and 30 wt. %, more preferably between 14 and 19.5 wt. %.

In yet another preferred embodiment of the invention, the epilatory mixture as a whole comprises between 2 and 35 wt. % of a starch hydrolysate. This has the advantage that the adhesive power as achieved can increase. It was found that the starch hydrolysate should preferably have a dextrose equivalent (DE) of at least 10; preferably, the DE of the starch hydrolysate is at most 75.

In order to arrive at an epilatory mixture having a beneficial or even optimal combination of properties such as viscosity, adhesive power and epilatory function, it may be necessary to carry out routine experiments within the ranges and combinations as given above. In particular, it was found to be beneficial to combine two or more or even all of the preferred embodiments as presented above. Thus, epilatory mixtures advantageously comprise not only a fructan but also a separately added monosaccharide or non-fructan disaccharide, and furthermore a $C_1$-$C_{12}$ diol such as methylpropanediol, water, and moreover a starch hydrolysate as well. Thus, according to a particularly preferred aspect of the invention, an epilatory mixture is provided and an epilatory composition comprising same, wherein said mixture is composed of (all percentages (%) herein are indicated in weight percent on total mixture being 100%, the (weight) percent of the saccharides being based on their dry matter content):

38% to 72% inulin having a DP ranging from 2 to 12,
2% to 25% fructose,
4% to 6% methylpropanediol,
7% to 22% starch hydrolysate with a dextrose equivalent value (D.E.) of minimum 10 and containing maximum 7% glucose,
0% to 1.5% glucose,
0% to 10% saccharose,
8% to 15% water, and wherein the sum of the water and methylpropanediol ranges from 14% to 19.5% weight of the epilatory mixture.

In a further preferred embodiment, the epilatory mixture is composed of

50% to 70% inulin having a DP ranging from 2 to 12,
4% to 20% fructose,
4% to 6% methylpropanediol,
7% to 15% starch hydrolysate with a D.E. of minimum 10 and containing maximum 7% glucose,
0% to 1% glucose,
0% to 7% saccharose,
9% to 15% water, and wherein the sum of the water and methylpropanediol ranges from 14.5% to 19.0% weight of the epilatory mixture.

In yet a further preferred embodiment, the epilatory mixture is composed of

60% to 70% inulin having a DP ranging from 2 to 12,
4% to 10% fructose,
4% to 6% methylpropanediol,
7% to 10% starch hydrolysate with a D.E. of minimum 10 and containing maximum 7% glucose,
0% to 0.5% glucose,
0% to 5% saccharose,
9% to 15% water, and wherein the sum of the water and methylpropanediol ranges from 14.5% to 19.0% weight of the epilatory mixture.

The invention further relates to epilatory compositions. Epilatory compositions according to the invention are understood to be compositions that comprise at least one epilatory mixture according to the present invention and may furthermore comprise other ingredients such as for example perfumes. Preferably the said other ingredients are ingredients that do not have a significant effect on epilatory (hair-removing) functionality. Preferably the epilatory composition according to the invention comprises at least 50%, 70, 80, 90 or 95% by weight, preferably at least 97% by weight, more preferably at least 99% by weight, of an epilatory mixture of the invention and may as indicated optionally further contain one or more conventional ingredients, such as for example perfume, a colouring agent, colour beads, and water soluble plant extracts. It is understood that an epilatory composition according to the invention also may consist essentially of an epilatory mixture according to the invention, which is namely the case when said composition only contains an epilatory mixture of the invention and does not contain any optionally further ingredients.

Herein the terms component(s) and ingredient(s), relating to the epilatory mixture and epilatory composition are used interchangeably.

As already indicated, inulin is a saccharide that is well known in the art. It is composed of polyfructose molecules of which the fructose units are exclusively or mainly connected to each other by β(2-1) fructosyl-fructose linkages and which may bear one terminal glucosyl unit. The polyfructose molecules can be linear, namely when all the fructose units are exclusively connected to each other by β(2-1) fructosyl-fructose linkages, or can be branched, namely when some fructose units of the polyfructose molecule are connected to each other by β(2-6) fructosyl-fructose linkages. The polyfructose molecules correspond to the general formulae $GF_n$ and $F_m$, wherein G represents a glucosyl unit, F a fructosyl unit, and n and m are integers that indicate the number of fructosyl units in the molecule. The values n+1 and m are referred to as degree of polymerisation (DP).

Inulin is synthesised by many plant species, can originate from bacterial activity, can be enzymatically synthesised in vitro, for example from sucrose and/or fructose, and can be obtained by partial hydrolysis of inulin molecules of plant or bacterial origin. Inulin can occur as a homodisperse mixture of inulin molecules, but commonly occurs as a polydisperse mixture of linear and/or branched polyfructose molecules. Inulin composed of molecules with a DP ranging between 2 and 10 is often also named oligofructose, fructo-oligosaccharide or inulo-oligo-saccharide.

By the term inulin as component of the epilatory mixture of the present invention is meant homodisperse and polydisperse inulin composed of linear and/or branched polyfructose molecules with a DP ranging from 2 to 75, preferably from 2 to 30, from 2 to 20, and most preferably from 2 to 12 or even from 2 to 9.

Inulin with a DP ranging as indicated can be obtained by conventional techniques from plant sources, by partial (acidic or enzymatic) hydrolysis of inulin from plant origin or from bacterial origin, and by enzymatic synthesis in vitro from sucrose and/or fructose. Homodisperse inulin can be conventionally obtained from polydisperse inulin. Typical plant sources for the manufacture of inulin include roots of chicory (*Cichorium intybus*), tubers of Dahlia and Jerusalem artichoke (*Helianthus tuberosus*), and the head (piña) of Blue Agave.

Inulin is commercially available in various grades. Some of these grades have a DP ranging from 2 to about 12 which can be obtained in various ways such as the partial, enzymatic hydrolysis of chicory inulin. One suitable inulin grade is available from ORAFTI S.A. (Belgium) under the trade name INUTEC® H25P (spray-dried powder with about 97% dry matter (d.m.) containing >93% [on d.m.] oligofructose with a DP from 2 to 9, mainly with a DP from 2 to 8, and maximally 7% in total of glucose, fructose and sucrose), INUTEC® H25 (aqueous liquid containing about 75% dry matter with a composition corresponding to the one of INUTEC® H25P), and INUTEC® H10 (aqueous liquid with 84.5% dry matter, containing [% on d.m.] 83 to 87% oligofructose of DP 2 to 9, mainly from 2 to 8, and in total 5% to 10% glucose and fructose and 5% to 9% sucrose.

Inulin of DP 2 to 75, 2 to 30, 2 to 20, 2 to 12, preferably of DP 2 to 9, including inulin obtained from plant sources, inulin obtained by enzymatic synthesis, as well as inulin obtained by partial hydrolysis and also named inulin hydrolysate, as well as the commercial grades thereof, and any mixtures thereof, are suitable for use as component of the epilatory mixture in accordance with the present invention. Usually a grade of inulin as available, in particular most commercial grades thereof, contain, apart from inulin itself, also glucose, fructose and sucrose. Only the amount of inulin molecules is taken into account for the definition of the amount of inulin in the epilatory mixture of the present invention, whereas the amounts of glucose, fructose and sucrose that may be present in said inulin grades are respectively counted together with the amounts of glucose, fructose and sucrose possibly separately added and thus present from other sources in the epilatory mixture.

As to the further components of the epilatory mixture of the invention, the following is noted. Fructose refers to the amount of fructose present in the inulin component in combination with the additional amount of fructose, typically added as crystalline fructose, that is required to reach a desired total amount of fructose. Methylpropanediol as preferred embodiment of a $C_1$-$C_{12}$ diol is obtainable as for example the commercial product MPDIOL LO (trade name of Lyondell Chemical Company, US). Starch hydrolysate is a product that is well known in the art. Starch hydrolysates that are preferred for use as a component of the epilatory mixture according to the present invention contain maximum 7% glucose (dextrose), preferably maximum 5% glucose, more preferably maximum 3% glucose, and have a dextrose equivalent value (D.E.) of minimum 10, preferably minimum 20, more preferably minimum 30. A typically suitable starch hydrolysate is for example a spray-dried glucose syrup (starch hydrolysate) with a D.E. of 35 to 40 obtained by enzymatic hydrolysis of starch, for example the commercial product C-DRY GL 01934 (trade name, available from Cargill) which is a spray-dried glucose syrup with a DE of 38 and a moisture content of 3% to 5%. Saccharose corresponds to the amount of saccharose present in the grade of inulin used in combination with any additional amount of saccharose that is required to reach a desired total amount of saccharose. Glucose corresponds to the total amount of glucose present in the grade of inulin and the starch hydrolysate used, in combination with any additional amount of glucose that is required to reach a desired total amount of glucose.

The epilatory mixture of the invention as well as the epilatory composition can be prepared according to conventional methods. For example, first the epilatory mixture can be prepared to which subsequently are added the optionally further ingredients, or one or more of the optionally further ingredients can already be added from the beginning to the components for the preparation of the epilatory mixture, or the ingredients of the epilatory mixture together with the further ingredients can be brought together and mixed to yield simultaneously the epilatory mixture and the epilatory composition.

According to a typical method for the preparation of the epilatory mixture, all the components of it in the required amounts are mixed under stirring and warming up to a temperature ranging preferably from 60° C. to 75° C., typically to about 65° C. It may be advantageous to replace the amount of water that possibly has been lost by evaporation during the manufacturing process. Accordingly, the process is preferably carried out in a closed container to avoid or minimise loss of water by evaporation. Subsequently, the warm mixture is allowed to cool down to about 30° C. to 40° C., typically to about 30° C. Before or during or subsequent to the cooling down the mixture, the optionally further ingredients are mixed into the mixture, yielding the epilatory composition. The resulting epilatory mixture or epilatory composition, present in the form of a viscous liquid, is then filled in conventionally appropriate containers.

A major advantage of the epilatory mixture and composition of the invention is that under temperature conditions ranging from 0° C. to 45° C. its viscosity can remain suitable for applying a layer onto the skin. Under said temperature conditions the epilatory composition of the invention can be easily spreadable and does not become too liquid in contact with the skin, while presenting an appropriate adherence to the skin as well as to the hair on the skin which results in an excellent epilatory performance. Accordingly, the epilatory composition of the invention is spreadable and applicable with an excellent epilatory performance over a wide temperature range, namely from 0° C. to 45° C., typically from 15° C. to 45° C. Furthermore, unlike most known epilatory compositions which are only effective up to about 40° C., the epilatory composition of the invention even presents excellent epilatory efficacy at a temperature ranging from 40° C. to 45° C. The applicability of the composition of the invention at a temperature ranging from 0° C. to 45° C. and its epilatory efficiency even at a temperature ranging from 40° C. to 45° C. constitute considerable advantages. Indeed, the epilatory composition of the invention can be conveniently used in a wide range of climates and circumstances.

A further advantage is that the epilatory composition of the invention may not need to be heated prior to its use. Accordingly, possible burns of the skin resulting from improper application conditions as sometimes occur during the application of warm sugar-based epilatory waxes, and possibly subsequent complications can be avoided.

Furthermore, possible rests of the epilatory composition remaining on the skin can easily be removed with water, including cold water, or with water and soap.

Still a further advantage of the epilatory composition of the invention is that the fructans comprised therein typically are renewable, non-toxic and biodegradable components which do not provoke chemical irritation of the skin or allergenic reactions.

Yet another advantage is that the epilatory composition of the invention can be conventionally applied to the skin and can be used by professionals as well as by non-professional people (individuals) for carrying out an epilatory treatment.

In a further aspect, the present invention relates to a method of use of the epilatory composition of the invention for removing unwanted hair from the skin, namely for epilating selected area's of the skin. In still a further aspect, the present invention relates to a method of use of the epilatory composition of the invention for carrying out an epilatory treatment.

According to these methods, a layer of the composition of the invention, typically a layer of a thickness ranging from 0.1 or 0.5 mm to 2, 3 or 5 mm, is applied to an area of the skin with unwanted hair, preferably in the direction of the hair growth. Shortly thereafter, preferable immediately thereafter, a paper strip or cloth strip is placed over the layer and pressed into it. Then the strip is removed by pulling it off, most preferably in a single fast motion, in the opposite direction of the hair growth. Remains on the skin of the composition can typically be easily removed with water or with water and soap. In case the epilation is not complete, the strip can be pressed again with the adhesive layer onto the treated skin area and removed again by pulling it off in a single fast motion in the opposite direction of the hair growth, or the complete epilatory treatment can be repeated. However, the epilatory efficiency of the composition of the invention is such that in most cases a satisfactory result can be obtained by one single epilatory treatment, namely one application of the composition in combination with one fast removal of the applied layer.

As is usual in epilatory treatments, the skin to be epilated has to be clean, dry, and free from cosmetic compositions such as creams. Accordingly, prior to the epilatory treatment the skin should preferably be commonly washed and dried. Furthermore, as done conventionally, the epilatory treatment should preferably be carried out on a rather small area of the skin at a time. Furthermore, to reduce possible pain and a possible reaction to the mechanical stress applied to the skin and the removal of the hair, after-care products can be used, including cold water, appropriate conventional oils, creams and lotions.

The application of the epilatory composition in a layer onto the skin can be done conventionally, for example from a container by means of a spatula, or by means of an appropriate applicator such as a roll-on applicator.

The epilatory composition of the invention is suitable for use in epilatory treatments of the human skin. However, it may also be used in a method for removing unwanted hair from the skin of a mammal—e.g. a companion animal such as a dog or a cat—and in a method for carrying out an epilatory treatment of an area of the skin of a mammal, for example when removal of the hair from that area is recommended or advantageous in case the animal is subjected to a medical treatment.

The invention is illustrated by the examples below, without being limited thereto.

In Table 1 below, the commercial components are indicated of several epilatory mixtures/compositions according to the invention, and in Table 2 below, the detailed composition of the epilatory mixtures/compositions of the examples of Table 1 is indicated with respect to the amounts of inulin, water, glucose, fructose and saccharose, being the total amounts of said ingredients taking into account the amounts that have possibly been added as such as a component and the amounts of said ingredients that are present in the various commercial components of the concerned epilatory mixture/composition.

The examples according to the invention are indicated by numbers 1-7; a comparative experiment not according to the invention is presented here under indicator A.

TABLE 1

| Example number | Commercial components (% in weight percent) | | | | | |
|---|---|---|---|---|---|---|
| | Inutec H25[1] | Inutec H25P[2] | Inutec H10 at 84.5% d.m.[3] | Fructose[4] | MPDIOL LO[5] | Glucose syrup[6] |
| 1 | 47.62 | 6.67 | 0.00 | 20.00 | 4.76 | 20.95 |
| 2 | 54.72 | 0.00 | 0.00 | 19.81 | 4.76 | 20.71 |
| 3 | 0.00 | 0.00 | 86.80 | 0.00 | 5.00 | 8.20 |
| 4 | 0.00 | 23.42 | 52.25 | 0.00 | 4.50 | 19.83 |
| 5 | 0.00 | 33.06 | 53.72 | 0.00 | 4.96 | 8.26 |
| 6 | 0.00 | 0.00 | 53.85 | 20.19 | 4.81 | 21.15 |
| 7 | 0.00 | 33.00 | 53.80 | 0.00 | 5.00 | 8.20 |
| A | 0.00 | 0.00 | 0.00 | 86.78[7] | 4.96 | 8.26 |

Legend to Table 1
[1]Inutec ® H25 (Trade name; Orafti, Belgium). Composition: inulin: 70.96%; glucose: 0.07%; fructose: 3.75%; saccharose: 0.22%; water: 25%.
[2]Inutec ® H25P (Trade name; Orafti, Belgium). Composition: inulin: 91.76%; glucose: 0.1%; fructose: 4.85%; saccharose: 0.29%; water: 3%.
[3]Inutec ® H10 (Trade name; Orafti, Belgium). Composition: water: 15.5% and 84.5% d.m., namely inulin: 72.5%; glucose: 1.01%; fructose: 4.65%; and saccharose: 6.34%;
[4]Crystalline fructose
[5]MPDIOL LO ®: trade name of Lyondell Chemical Company (US) for methylpropanediol
[6]Glucose syrup: C-DRY GL 01934, trade name of Cargill for spray-dried glucose syrup with a DE of 38 and a moisture content of 3% to 5%.
[7]73.78% fructose plus 13.0% water.

TABLE 2

| Example number[1] | Components (% in weight percent) | | | | |
|---|---|---|---|---|---|
| | inulin[2] | water | glucose | fructose | saccharose |
| 1 | 39.91 | 12.93 | 0.46 | 22.11 | 0.12 |
| 2 | 38.83 | 14.50 | 0.46 | 21.86 | 0.12 |
| 3 | 62.93 | 13.77 | 1.04 | 4.04 | 5.50 |
| 4 | 59.37 | 9.60 | 0.95 | 3.57 | 3.38 |
| 5 | 69.28 | 9.66 | 0.74 | 4.10 | 3.50 |
| 6 | 39.04 | 9.19 | 0.97 | 22.69 | 3.41 |
| 7 | 69.29 | 9.65 | 0.74 | 4.10 | 3.51 |
| A | 0.00 | 13.00 | 0.00 | 73.78 | 0.00 |

Legend to Table 2
[1]The example number corresponds to that of table 1
[2]Inulin of DP ranging from 2 to 9.

The mixtures/compositions described in tables 1 and 2 have been tested for their epilatory efficacy according to the typical procedure described above, according to which the epilatory composition, having a temperature of 23° C., has been applied on an area of the arm, subsequently covered with a paper strip that is pressed into the layer, and then removed by pulling off the paper strip rapidly in a single motion against the direction of the hair growth. The rating applies to one single treatment. The efficacy of the epilatory effect has been rated with a value ranging from 10 (excellent effect) to 0 (zero effect) as follows:

| | |
|---|---|
| rating 10 | all hair (long and short hair) is removed |
| rating 9 | 1 hair is left on the concerned area |
| rating 8 | a few hairs remain (these hairs are removed when the used strip is applied a second time) |
| rating 7 | about ¼ of the hairs remain on the skin |
| rating 1 | some pulling on the hair is noticed, but the hair is not removed |
| rating 0 | no effect on the hairs is noticed. |

Only epilatory compositions presenting a rating 8 to 10 are considered appropriate for commercial epilatory purposes.

The epilatory results of compositions of the invention are presented in Table 3 below.

TABLE 3

| Example Number[1] | Rating value of the epilatory efficiency from 0 (no effect) to 10 (excellent effect) |
|---|---|
| 1 | 8 |
| 2 | 9 |
| 3 | 10 |
| 4 | 9 |
| 5 | 10 |
| 6 | 8 |
| 7 | 10 |
| A | 0 |

Legend to Table 3
[1]The numbers of examples and comparative experiment correspond to the ones of Table 1 and Table 2 above.

The above results demonstrate that the epilatory mixtures/compositions according to the present invention present excellent epilatory properties, whereas the comparative experiment showed that a fructose-based formulation does not function at room temperature.

The invention claimed is:

1. Epilatory mixture for removing undesired hair, comprising between 25 and 82 wt. % fructan, between 1 and 45 wt. % of at least one separately added monosaccharide, between 0.5 and 15 wt. % of a C1-C12 diol, and between 2 and 35 wt. % of a starch hydrolysate, said epilatory mixture exhibiting epilatory efficacy and adherence to the skin and hair over a temperature range of from 0° C. to 45° C.

2. Epilatory mixture according to claim 1, wherein the fructan comprises inulin.

3. Epilatory mixture according to claim 1, wherein the degree of polymerisation (DP) of the fructan ranges from 2 to 75.

4. Epilatory mixture according to claim 1, wherein the $C_1$-$C_{12}$-diol is methylpropanediol.

5. Epilatory mixture according to claim 1, wherein the mixture further comprises between 1 and 25 wt. % water.

6. Epilatory mixture according to claim 1, wherein the mixture further comprises water and a $C_1$-$C_{12}$-diol, and the sum of the water and $C_1$-$C_{12}$— diol ranges from 10 to 30 wt. %.

7. Epilatory composition comprising at least 90 wt. % on total composition of an epilatory mixture defined in claim 1, and optionally one or more further ingredients.

8. Epilatory composition according to claim 7, consisting essentially of an epilatory mixture defined in claim 1.

9. Epilatory composition according to claim 7, wherein said further ingredients comprise a perfume, a colouring agent, colour beads and water soluble plant extracts.

10. Epilatory mixture for removing undesired hair, said epilatory mixture exhibiting adherence to the skin and hair over a temperature range of from 0° C. to 45° C., wherein the mixture contains:
38% to 72% inulin having a DP ranging from 2 to 12,
2% to 25% fructose,
4% to 6% methylpropanediol,
7% to 22% starch hydrolysate with a dextrose equivalent value (D.E.) of minimum 10 and containing maximum 7% glucose,
0% to 1.5% glucose,
0% to 10% saccharose,
8% to 15% water,
wherein the sum of the water and methylpropanediol ranges from 14% to 19.5% of the epilatory mixture and wherein the sum of the weight percentages adds to 100%.

11. Epilatory mixture according to claim 10, containing:
50% to 70% inulin having a DP ranging from 2 to 12,
4% to 20% fructose,
4% to 6% methylpropanediol,
7% to 15% starch hydrolysate with a D.E. of minimum 10 and containing maximum 7% glucose,
0% to 1% glucose,
0% to 7% saccharose,
9% to 15% water,
wherein the sum of the water and methylpropanediol ranges from 14.5% to 19.0% weight of the epilatory mixture.

12. Epilatory mixture according to claim 11, wherein the inulin is oligofructose with a DP ranging from 2 to 9.

13. Epilatory mixture according to claim 11, wherein the starch hydrolysate contains maximum 5% glucose.

14. Epilatory mixture according to claim 11, wherein the starch hydrolysate contains maximum 3% glucose.

15. Epilatory mixture according to claim 11, wherein the starch hydrolysate has a D.E. of minimum 20.

16. Epilatory mixture according to claim 11, wherein the starch hydrolysate has a D.E. of minimum 30.

17. Epilatory mixture according to claim 10, containing:
60% to 70% inulin having a DP ranging from 2 to 12,
4% to 10% fructose,
4% to 6% methylpropanediol,
7% to 10% starch hydrolysate with a D.E. of minimum 10 and containing maximum 7% glucose,
0% to 0.5% glucose,
0% to 5% saccharose,
9% to 15% water,
and wherein the sum of the water and methylpropanediol ranges from 14.5% to 19.0% weight of the epilatory mixture.

18. Epilatory mixture according to claim 10, wherein the inulin is oligofructose with a DP ranging from 2 to 9.

19. Epilatory mixture according to claim 10 wherein the starch hydrolysate contains maximum 5% glucose.

20. Epilatory mixture according to claim 19 wherein the starch hydrolysate contains maximum 3% glucose.

21. Epilatory mixture according to claim 10, wherein the starch hydrolysate has a D.E. of minimum 20.

22. Epilatory mixture according to claim 21, wherein the starch hydrolysate has a D.E. of minimum 30.

23. A method for the removal of hair from the skin comprising applying to the skin needing treatment the epilatory mixture defined in claim 1.

24. The method according to claim 23, wherein the epilatory mixture is applied in a layer on an area of the skin, the layer is subsequently covered with a paper strip or textile strip which is pressed onto said layer, and the strip is then removed by pulling it off in a single fast motion in the direction opposite to the hair growth taking with it unwanted hair that was present on the treated skin area.

25. The method according to claim 23, wherein the mixture is applied to human skin or the skin of a companion animal.

26. An epilatory treatment method comprising applying the epilatory mixture defined in claim 1 to the skin.

27. The method according to claim 26, wherein the composition is applied to human skin or the skin of a companion animal.

28. An epilatory treatment method comprising applying the epilatory composition of claim 7 to the skin.

29. The method according to claim 28, wherein the epilatory composition is applied in a layer on an area of the skin, the layer is subsequently covered with a paper strip or textile strip which is pressed onto said layer, and the strip is then removed by pulling it off in a single fast motion in the direction opposite to the hair growth taking with it unwanted hair that was present on the treated skin area.

\* \* \* \* \*